(12) United States Patent
Al-Hossary

(10) Patent No.: US 7,645,257 B2
(45) Date of Patent: Jan. 12, 2010

(54) INTRAVENOUS DEVICE AND METHOD FOR REMOVING OF MYOGLOBIN FROM CIRCULATING BLOOD

(76) Inventor: Amr Ali Al-Hossary, 12 El-Morsy St., Ard El-Etr, Al-sananeyyah, Post Code 34713 Damietta (EG)

( * ) Notice: Subject to any disclaimer, the term of this patent is extended or adjusted under 35 U.S.C. 154(b) by 0 days.

(21) Appl. No.: 10/578,673

(22) PCT Filed: Nov. 9, 2004

(86) PCT No.: PCT/EG2004/000046

§ 371 (c)(1),
(2), (4) Date: May 9, 2006

(87) PCT Pub. No.: WO2005/044329

PCT Pub. Date: May 19, 2005

(65) Prior Publication Data

US 2007/0082396 A1    Apr. 12, 2007

(30) Foreign Application Priority Data

Nov. 11, 2003   (EG)   ............................. 2003111025

(51) Int. Cl.
*C12N 5/16* (2006.01)
*A61M 5/31* (2006.01)

(52) U.S. Cl. .................... 604/35; 604/27; 604/192; 435/326

(58) Field of Classification Search ............... None
See application file for complete search history.

(56) References Cited

U.S. PATENT DOCUMENTS

| | | | | |
|---|---|---|---|---|
| 2,767,703 A | * | 10/1956 | Nieburgs | ............ 600/562 |
| 3,452,742 A | * | 7/1969 | Muller | ............ 600/585 |
| 4,494,531 A | * | 1/1985 | Gianturco | ............ 606/200 |
| 5,353,792 A | * | 10/1994 | Lubbers et al. | ............ 600/311 |
| 5,573,957 A | * | 11/1996 | Cardone et al. | ............ 436/518 |
| 5,810,810 A | * | 9/1998 | Tay et al. | ............ 606/50 |
| 6,063,085 A | * | 5/2000 | Tay et al. | ............ 606/50 |
| 6,264,627 B1 | * | 7/2001 | Liska et al. | ............ 604/29 |
| 6,863,790 B1 | * | 3/2005 | Moini et al. | ............ 204/452 |
| 6,942,634 B2 | * | 9/2005 | Odland | ............ 604/6.09 |
| 7,026,280 B2 | * | 4/2006 | Mendelsohn et al. | ............ 514/2 |
| 7,232,689 B2 | * | 6/2007 | Pawliszyn | ............ 436/178 |
| 7,259,019 B2 | * | 8/2007 | Pawliszyn et al. | ............ 436/178 |
| 7,384,794 B2 | * | 6/2008 | Pawliszyn | ............ 436/178 |
| 2002/0147129 A1 | * | 10/2002 | Mendelsohn et al. | ............ 514/2 |
| 2002/0160428 A1 | * | 10/2002 | Sundrehagen | ............ 435/7.9 |
| 2003/0187367 A1 | * | 10/2003 | Odland | ............ 600/573 |
| 2004/0186407 A1 | * | 9/2004 | Walker et al. | ............ 604/4.01 |
| 2004/0248181 A1 | * | 12/2004 | Stenken et al. | ............ 435/6 |
| 2005/0154035 A1 | * | 7/2005 | Lieberburg | ............ 514/379 |
| 2005/0165342 A1 | * | 7/2005 | Odland | ............ 604/5.01 |
| 2005/0287679 A1 | * | 12/2005 | Pawliszyn | ............ 436/174 |
| 2006/0079740 A1 | * | 4/2006 | Silver et al. | ............ 600/309 |
| 2008/0176271 A1 | * | 7/2008 | Silver et al. | ............ 435/29 |

* cited by examiner

*Primary Examiner*—Robert B Mondesi
*Assistant Examiner*—Ginnyallen Portner

(57) ABSTRACT

Prevention of Acute Renal Failure following myoglobinemia in cases of rhabdomyolysis by means of trapping myoglobin released to circulation following striated muscles injury using a temporary intravenous filter, hence prophylaxis of Acute Renal Failure, which commonly follows this situation. It is directed to all cases of rhabdomyolysis especially for "In situ prevention" in cases of disasters, crush injuries, and reperfusion injury in a limb.

13 Claims, 1 Drawing Sheet

INTRAVENOUS DEVICE AND METHOD FOR REMOVING OF MYOGLOBIN FROM CIRCULATING BLOOD

TECHNICAL FIELD

Myoglobinemia means the presence of myoglobin (an 18,800-Dalton Oxygen carrier protein (ptn) present in the sarcoplasma of muscles).

It happens in some cases, we are concerned here with acute traumatic causes of crushing muscles, e.g. crush syndrome or falling objects in disasters.

Rhabdomyolysis is the breakdown of striated muscles. It leads to the release of intra muscular components to the interstitial fluid (I.S.F.) One of the key compounds released is myoglobin (oxygen carrier resembles hemoglobin but with only one haeme moiety).

Other components are Calcium, phosphorus, potassium, and nucleosides (metabolized later in the liver into xanthine, hypoxanthine and uric acid)

Most important causes of rhabdomyolysis are:

1) Trauma and compression in accidents, crush syndrome, earth quakes, war disasters, and long term confinement in the same position (e.g. orthopedic problems and interventions necessitating specific position for long time)

2) Occlusion of muscular vessels: thrombosis, occlusion, or clamping

3) Drugs & toxins: alcohol, heroin

Pathology of Myolysis:

Muscle lysis occurs by 3 ways:

Changes in Cellular Metabolism:

Ending in calcium entrance and so persistent contraction & cell death & free oxygen radicals production. It is invaded by activated neutrophils too which produce protons & free radicals Reperfusion Injury In ischemic injury, most of the damage happens after restoration of blood flow; leukocytes migrate into the damaged tissue only after reperfusion. and free radical production starts only when Oxygen is amply available Compartment Syndrome If the energy dependant transcellular pump system ,the muscle cells swell and so inter compartmental pressure rises [>30 Millimeter Mercury (mmHg) produce clinically significant muscle ischemia, in hypotensive patients, even lower compartmental pressure will cause reperfusion problems]

Metabolic Derangement During Rhabdomyolysis

The release of constituents of necrotic muscles results in alteration of plasma concentration of several compounds. If Acute Renal Failure (A.R.F.) develops, it aggravates the condition Myoglobin: it is our enemy here Fluids: Massive amounts of fluids accumulate in the affected limb (up to 10 liters per limb). Loss of that amount may lead to shock, hypematremia, and deterioration of renal function if not replaced Potassium: massive amount of potassium is released (which can't be eliminated by the kidney if ARF develops)

Calcium and phosphorus: released & may deposit in tissues

Nucleosides: released from disintegerating muscle cell nuclei to the blood and metabolized in liver into xanthine, hypoxanthine, and uric acid Organic acids: their release (in addition of the production of uric acid from metabolized nucleosides) cause a high anion gap Pathophysiology of ARF:

Myoglobin is easily filtered through the glomerular basement membrane. Water is progressively reabsorbed into the tubules and so the concentration of myoglobin rises proportionately until it precipitates & causes obstructive cast formation.

Low pH (Acidosis) favors the precipitation of myoglobin & uric acid. Haeme centre of myoglobin initiates lipid peroxidation and renal injury. Degradation of intratubular myoglobin results in the release of free Iron which catalyze the release of free radicals and further enhances ischemic damage That leads to death in 20-50% of cases

BACKGROUND ART

Prevention and Treatment:

The main aim of therapy is to prevent factors which cause ARF, i.e. volume depletion, aciduria, tubular obstruction, and free radicals production That is tried through:

A) Opening a line even before the patient is still being extricated.

B) Administering fluids, mannitol, sodium bicarbonates, etc. through this line.

Fluids are added up to 10 Liters/limb to prevent hypovolemia. In cases in which muscles are compressed due to trauma, administration of fluids must begin before the victim is extricated from under the rubble Sodium Bicarbonates: useful in correcting acidosis, and so to prevent precipitation of myoglobin in renal tubules.

It also reduces the risk of hyperkalemia.

Mannitol: used because 1) it increases Renal Blood Flow (RBF) and Glomerular Filtration Rate (GFR)
2) it is an osmotic agent that attracts fluids from interstitial compartment, and thus counterbalancing hypovolemia and reducing muscular swelling and nerve compression
3) it is an osmotic diuretic that increases urine flow and prevent cast formation
4) it scavenges free radicals Extracorporial Blood Purification:

Once ARF of severe hyperkalemia and acidosis are established, patient needs dialysis.

It is supposed to be the only hope for patients for life.

Haemodialysis is used.

Peritoneal dialysis is not performed.

Plasma exchange has no demonstrated benefit because the metabolic turn over of myoglobin is fast.

During reperfusion operations in ischemic cases (e.g. empolectomy), venotomy is described to evacuate the first 500 ml of venous blood returning after removing the obstruction to the arterial tree in order to get rid of most of the harmful compounds in the blood

DEFECT IN BACKGROUND ART

Wasting 500 cc (cubic centimeter) is not accepted, especially for traumatized patients who are already bleeding as it would aggravate their hypovolemia Peritoneal dialysis is not possible to patients with traumatized abdomen and any way it would be inefficient.

Extra Corporial blood purification is a supportive treatment aiming at passing the ARF period but not directed towards counteracting the cause of the problem Also it requires either transporting the ill traumatized patients to a near by well equipped place, or to transport a full equipped dialysis unit to the site of disaster.

It also requires continuous anticoagulation (notice that we are talking about traumatized patients)

Death Rate hasn't shown a considerable rise during the last 20 years (even with dialysis), which makes prevention of ARF an absolute priority

DISCLOSURE OF INVENTION

New Concepts

1) Directing the effort towards trapping myoglobin itself while it is still in the venous blood stream before it reaches the heart to be bumped all over the body and cause its damage by means of an attracting filter.

That method is directed towards the main cause of problem, NOT towards passing the period of its harmful effect.

That increases the efficiency of this method over other methods depending on treating the effect of myoglobin excess in the blood.

2) That filter is easily administered (same method of introducing a central cannula) which is a routine procedure being already done in such cases.

3) The filter is then removed almost instantaneously before it can have chance to cause either anaphylaxis or thrombus, It even will be coated with myoglobin all around (which is a normal blood component) and so will never cause anaphylaxis if left for a time more than required (e.g. Because of being busy with large number of victims in cases of disasters).

4) The procedures of introducing and removing the filter are simple percutaneous procedures without complicated invasive techniques which need highly qualified personnel.

5) The functionally active area of the filter is ALL its length already present in the blood stream from its point of introduction till its end; that's because it doesn't trap the myoglobin returning from the injured limb only, but also from the major circulation all over the body through both vinae cavae 6) This procedure is directed towards all cases of rhabdomyolysis, especially for "Insitu Prevention of ARF" in cases of Disasters, crush injuries, reperfusion injury in a limb either During operative reperfusion or in cases of disasters

Details

Trapping myoglobin is achieved by the introduction of a myoglobin trapping filter in the vein draining the affected area or limb (e.g. the femoral vein in case of lower limb) or through the Internal Jugular Vein (I.J.V.) in a way similar to that of introducing an Inferior Vena Cava (I.V.C.) filter which protects from empolization in case of Deep Venous Thrombosis (D.V.T.)

As shown in FIG. 1, that filter is a rod consisting of a central axis of any suitable wire(1), sheathed by latex (2) coated with antimyoglobin antibodies(3).

It can be introduced to the I.J.V. through an opening made by a cannula(4). It should be introduced in the same procedure of opening I.V. line, before extrication of the victim.

It begins to function just as it is introduced into the blood stream. If some myoglobin particles escaped the whole length of the filter and reached the heart, it could be trapped in the next blood circulation (notice that it's present along the I.J.V., the Superior Vena Cava, right atrium, I.V.C. & may be the femoral vein).

It should be left in place until the antimyoglobin antibodies are saturated or until the danger is over, Then it should be removed.

Another one may be introduced if needed either simultaneously or consequently.

DESCRIPTION OF DRAWINGS

1) A central wire
2) Latex coat
3) Antimyoglobin antibodies
4) A Cannula

Where Appropriate to Carry Out this Method

Figure 1:
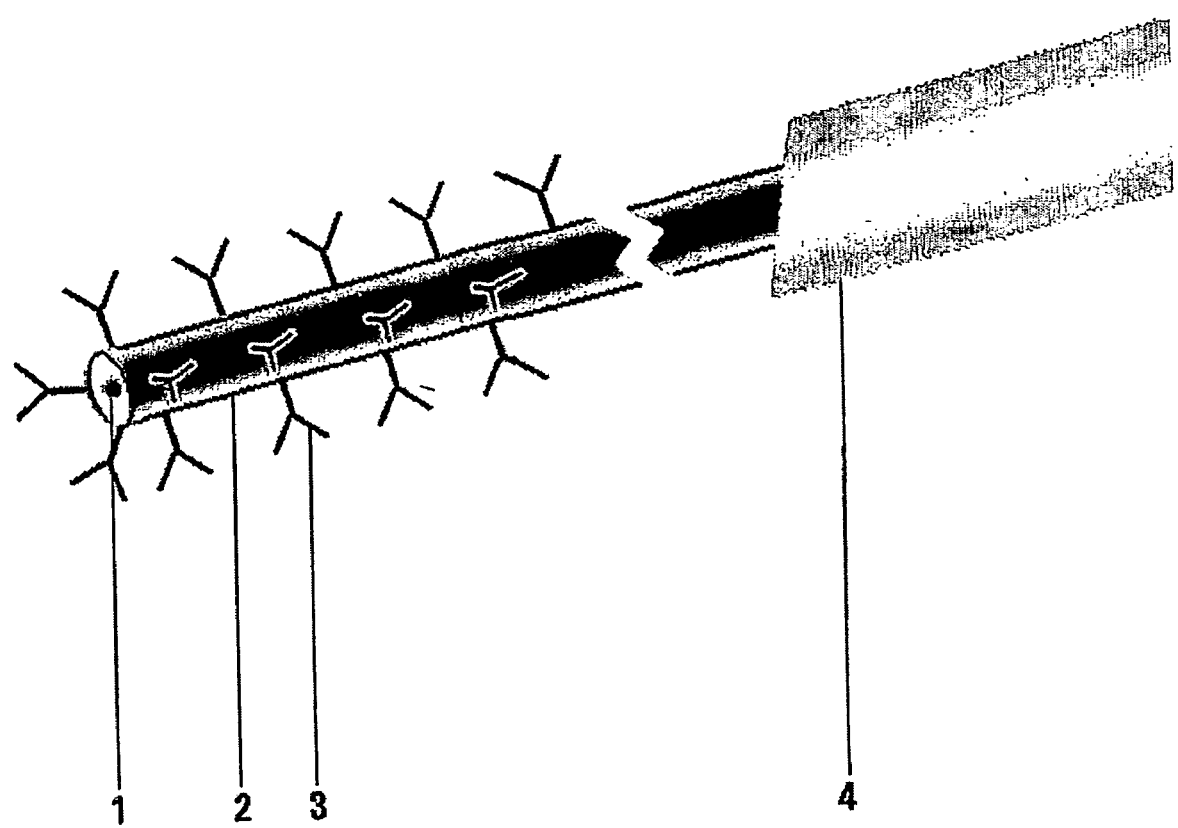

This method is directed to all cases of Rhabdomyolysis, especially for "In situ prevention" in cases of disasters; crush syndrome; and "reperfusion injuries.

INDUSTRIAL APPLICABILITY

Using antibodies coated latex particles is a commonly used technique in medical field.

Latex is supported in many forms and can be ordered as needed.

Also antimyoglobin antibodies are already available in the market for various uses.

Wide scale usage of this device would reduce its cost, which is—in relation to human life—very cheap.

Unclear Terms Meanings/Definition

| # | Term | Meaning/Definition |
| --- | --- | --- |
| i. | I.V. (title) | Intravenous |
| ii. | I.S.F. (page 1) | Interstitial Fluid |
| iii. | mmHg (page 2) | Millimeter Mercury |
| iv. | A.R.F (page 2) | Acute Renal Failure |
| v. | RBF (page 4) | Renal Blood Flow |
| vi. | GFR (page 4) | Glomerular Filtration Rate |
| vii. | C.C. (page 6) | Cubic Centimeter |
| viii. | I.J.V. (page 8) | Internal Jugular Vein |
| ix. | I.V.C. (page 8) | Inferior Vena Cava |
| x. | D.V.T. (page 8) | Deep Venous Thrombosis |
| xi. | S.V.C. (page 8) | Superior Vena Cava |

The invention claimed is:

1. An intravenous device comprising of a rod of a shape and size for insertion into a vein, the red being coated with a sheath, and the sheath being coated with anti-myoglobin antibodies able to remove myoglobin from circulating blood.

2. The intravenous device of claim 1, wherein the rod is a wire.

3. The intravenous device of claim 1, wherein the sheath is latex.

4. The intravenous device of claim 1, wherein the anti-myoglobin antibodies are latex particle immobilized anti-myoglobin antibodies.

5. A cannula comprising the intravenous device of claim 4.

6. The cannula of claim 5, wherein the cannula comprises a tip.

7. The cannula of claim 6, wherein the cannula is a cylindrical shape with a central core into which the intravenous device is inserted, wherein the intravenous device can protrude from the tip end of the cannula.

8. The cannula of claim 7, wherein the antimyoglobin antibodies are coated over the whole surface area that protrudes from the tip end of the cannula.

9. A method comprising the steps of:

Percutaneously introducing the cannula of claim 5 into a vein of a patient,

Removing the intravenous device from the patient after a period of time during which myoglobin is trapped by the antimyoglobin antibodies, Reintroducing another intravenous device through the central core of cannula into the patient's vein to trap additional circulating myoglobin as needed, then removing the cannula and intravenous device from the patient.

10. The method of claim 9, wherein the patient is at risk of Acute Renal Failure, rhabdomyolysis, or myoglobinemia.

11. The method of claim 10, wherein the risk of Acute Renal Failure is associated with earthquakes, orthopedic problems, alcohol and heroin use, occlusion of muscular vessels, crush injuries, compartment syndrome, or reperfusion injury in a limb.

12. The method of claim 11, wherein the reperfusion injury in a limb is associated with operative reperfusion.

13. The method of claim 9, wherein the vein is the vina cava, internal jugular vein, femoral vein.

* * * * *